United States Patent
Dawoodjee

(10) Patent No.: US 11,925,326 B1
(45) Date of Patent: Mar. 12, 2024

(54) PORTABLE HANDHELD ENDOSCOPIC IMAGE AND VIDEO CAPTURE AND DISPLAY SYSTEM

(71) Applicant: John Dawoodjee, Canoga Park, CA (US)

(72) Inventor: John Dawoodjee, Canoga Park, CA (US)

( * ) Notice: Subject to any disclaimer, the term of this patent is extended or adjusted under 35 U.S.C. 154(b) by 0 days.

(21) Appl. No.: 17/373,353

(22) Filed: Jul. 12, 2021

Related U.S. Application Data

(60) Provisional application No. 63/051,524, filed on Jul. 14, 2020.

(51) Int. Cl.
| | |
|---|---|
| *H04N 7/18* | (2006.01) |
| *A61B 1/00* | (2006.01) |
| *A61B 1/04* | (2006.01) |
| *H04N 7/015* | (2006.01) |
| *H04N 23/51* | (2023.01) |
| *H04N 23/54* | (2023.01) |
| *H04N 23/60* | (2023.01) |
| *H04N 23/50* | (2023.01) |

(52) U.S. Cl.
CPC .......... *A61B 1/042* (2013.01); *A61B 1/00034* (2013.01); *A61B 1/00066* (2013.01); *A61B 1/00121* (2013.01); *H04N 7/015* (2013.01); *H04N 7/183* (2013.01); *H04N 23/51* (2023.01); *H04N 23/54* (2023.01); *H04N 23/60* (2023.01); *H04N 23/555* (2023.01)

(58) Field of Classification Search
CPC . A61B 1/042; A61B 1/00034; A61B 1/00066; A61B 1/00121; H04N 5/2252; H04N 5/2253; H04N 5/232; H04N 7/015; H04N 7/183; H04N 2005/2255

See application file for complete search history.

(56) References Cited

U.S. PATENT DOCUMENTS

| | | | | |
|---|---|---|---|---|
| 3,186,878 A | * | 6/1965 | Filander | H01M 50/20 |
| | | | | 429/97 |
| 5,401,591 A | * | 3/1995 | Bishay | H01M 50/213 |
| | | | | 429/97 |
| 2013/0072923 A1 | * | 3/2013 | Behnke, II | A61B 18/1815 |
| | | | | 606/33 |

FOREIGN PATENT DOCUMENTS

| | | | | |
|---|---|---|---|---|
| CN | 107854104 A | * | 3/2018 | |
| CN | 209690617 U | * | 11/2019 | |
| DE | 112009000536 T5 | * | 2/2011 | ......... A61B 1/00022 |

(Continued)

*Primary Examiner* — Michael Lee
(74) *Attorney, Agent, or Firm* — Plager Schack LLP; Mark H. Plager; Stephen Hallberg

(57) ABSTRACT

A handheld C-mount HD endo-camera is disclosed which records images/videos, is able to transmit the images/videos to adaptable secondary monitor with removable Lithium-ion battery and attached to any rigid, semi-rigid, or flexible endoscope to allow a surgeon to see images and videos while manipulating the endoscope. The handheld C-mount HD endo-camera is portable, provides C-mount HD images, is adaptable with secondary devices and powered with a removable and rechargeable Lithium-ion battery. Attached to any rigid, semi-rigid, or flexible endoscope, a surgeon can see the surgical field directly on the camera monitor in their hand because the handheld C-mount HD endo-camera is self-contained and portable, thereby obviating the need for a video tower and associated conventional viewing equipment.

14 Claims, 4 Drawing Sheets

(56) References Cited

FOREIGN PATENT DOCUMENTS

TW 201110926 A * 4/2011 ......... A61B 1/00022

* cited by examiner

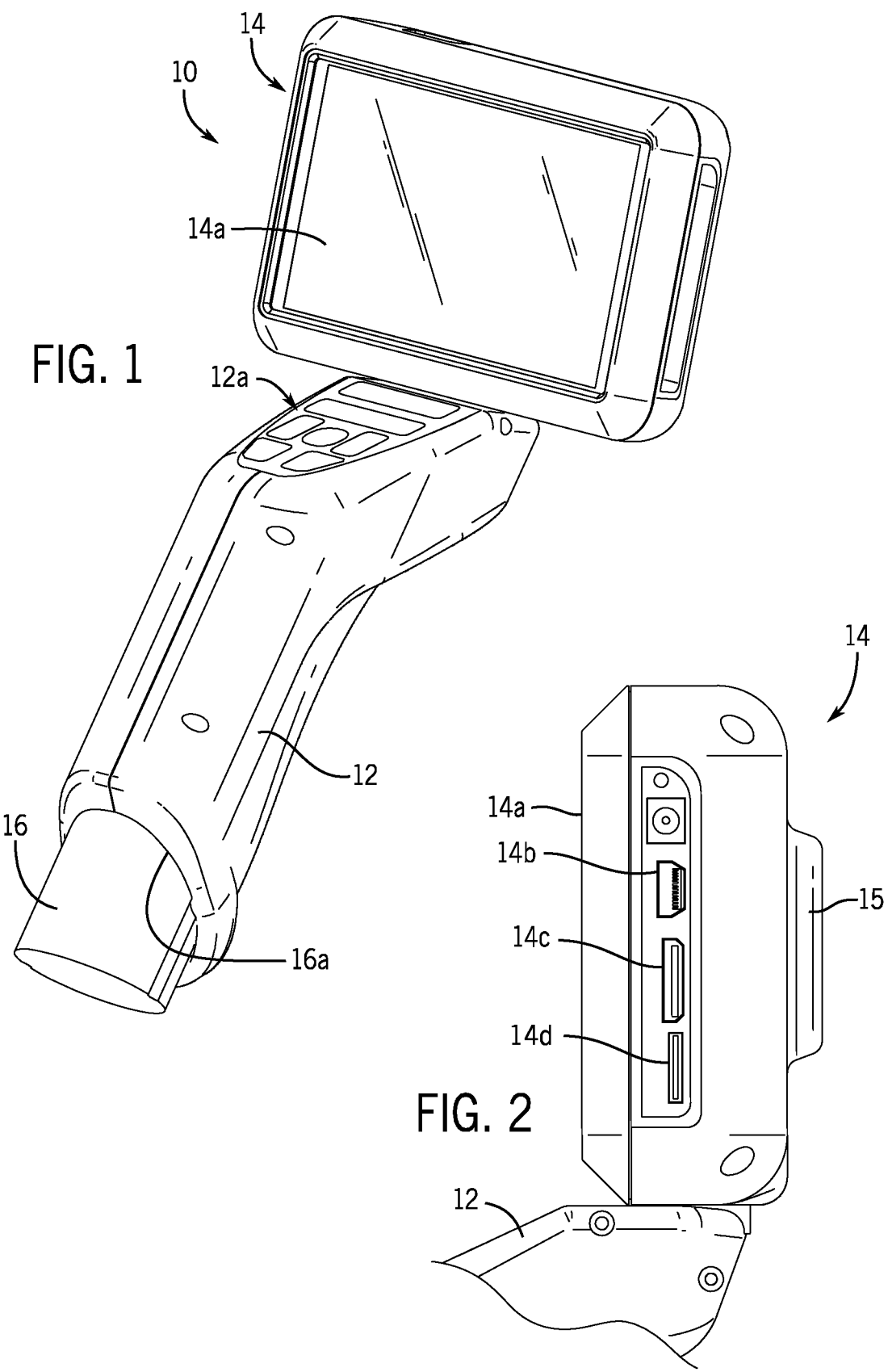

PORTABLE HANDHELD ENDOSCOPIC IMAGE AND VIDEO CAPTURE AND DISPLAY SYSTEM

CLAIM OF BENEFIT TO PRIOR APPLICATION

This application claims benefit to U.S. Provisional Patent Application 63/051,524, entitled "HANDHELD PORTABLE C-MOUNT HD ENDO-CAMERA THAT CAPTURES IMAGES, RECORDS VIDEOS, AND TRANSMITS THE IMAGERY AND VIDEOS TO AN ADAPTABLE SECONDARY MONITOR WITH REMOVABLE LITHIUM-ION BATTERY," filed Jul. 14, 2020. The U.S. Provisional Patent Application 63/051,524 is incorporated herein by reference.

BACKGROUND

Embodiments of the invention described in this specification relate generally to a portable handheld endoscopic image and video capture and display system, and more particularly, to a handheld C-mount high definition (HD) endoscopic camera ("endo-camera") that is attached to any rigid, semi-rigid, or flexible endoscope used by a surgeon and captures images, records videos, and is able to transmit the imagery and videos to an adaptable secondary monitor with removable Lithium-ion battery while the surgeon is manipulating the endoscope.

To visualize an endoscopic procedure a surgeon attaches an endoscope to a 1080p HD camera head that transmits images and video through a long flexible cable to a camera control unit (CCU). A light source is connected to the endoscope light post to illuminate the surgical field. Video in real time is transmitted from the camera head to the CCU and then to a monitor where the surgeon can see the camera image. The monitor is often placed at the top of a video tower forcing the surgeon to look up at the monitor and not the patient. The surgeon is required to manipulate the endoscope viewing the monitor and not his/her hands. A real-time video enhancement device designed to amplify visualization by improving clarity, contrast and detail is often connected to the CCU. The still images and videos are saved to the CCU by another electrical unit.

A conventional video tower is used to hold the camera head, CCU, light source, image clarifier and monitor. A power strip is used to provide sufficient electricity for all the necessary equipment. While some video towers have casters, it is unwieldy moving the video tower to another location. The devices in a video tower (camera head, CCU, light source, image clarifier, and monitor) must be fully operational and compatible. The video tower devices produce inconsistent quality images/videos and are difficult to transfer to secondary devices. Additionally, multiple sources of electricity are required and the conventional (existing) options are not portable.

Therefore, what is needed is a portable imaging endoscope device that is battery powered and is capable of providing high definition images and video and which includes or is adaptable to include a secondary monitor, which when attached to an endoscope, provides a surgeon a convenient and easy front view of a screen to view images and videos while manipulating the endoscope.

BRIEF DESCRIPTION

A novel portable handheld endoscopic image and video capture and display system is disclosed. In some embodiments, the portable handheld endoscopic image and video capture and display system comprises a handle, a keyboard, and a camera unit. In some embodiments, the camera unit comprises an endoscopic camera (also referred to as an "endo-camera"). In some embodiments, the camera unit comprises the endoscopic camera and a primary camera monitor (also referred to as a "display screen"). In some embodiments, the endoscopic camera attaches to an endoscope to capture images and record videos in connection with a patient. In some embodiments, the endoscopic camera captures imagery and video in high definition ("HD"). In some embodiments, the endoscopic camera captures imagery and video in ultra-high definition ("UHD" or "4K" resolution). In some embodiments, the camera unit transmits the images and videos to the camera monitor for display on the display screen while a surgeon is manipulating the endoscope. In some embodiments, the camera unit transmits the images and videos to an adaptable, detached secondary monitor while the surgeon is manipulating the endoscope.

In some embodiments, the portable handheld endoscopic image and video capture and display system is a handheld portable C-mount high definition (HD) endoscopic camera ("endo-camera"). In some embodiments, the handheld portable C-mount high definition (HD) endoscopic camera attaches to any rigid, semi-rigid, or flexible endoscope used by an operator, such as a surgeon during endoscopic surgery. In some embodiments, the handheld portable C-mount high definition (HD) endoscopic camera transmits the captured images and recorded videos to the camera monitor for display on the display screen in realtime while the endoscope is being manipulated. In some embodiments, the handheld portable C-mount HD endo-camera is self-contained and portable in a way that allows the operator (surgeon) to hold the handle in a manner that aligns a field of view of the endoscopic camera to a particular surgical field. In this way, the surgeon or other operator of the handheld portable C-mount HD endo-camera can see the surgical field directly on the display screen of the camera monitor without obtrusive and bulky video towers (camera head, CCU, light source, image clarifier, monitor and power strip), external power cords (tripping hazard), and other interfering elements of the conventional systems.

In some embodiments, the handheld portable C-mount HD endo-camera is adaptable with secondary devices via one or more input/output ports of the camera unit. In some embodiments, the handheld portable C-mount HD endo-camera is powered by a removable and rechargeable battery. In some embodiments, the removable and rechargeable battery comprises a Lithium-ion battery. In some embodiments, the Lithium-ion battery is positioned within a battery socket of the handle when powering the handheld portable C-mount HD endo-camera.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having thus described the invention in general terms, reference is now made to the accompanying drawings, which are not necessarily drawn to scale, and which show different views of different example embodiments, and wherein:

FIG. 1 conceptually illustrates a perspective view of a portable handheld endoscopic image and video capture and display system in some embodiments.

FIG. 2 conceptually illustrates a detail side elevation view of the portable handheld endoscopic image and video capture and display system in some embodiments.

Figure 3:
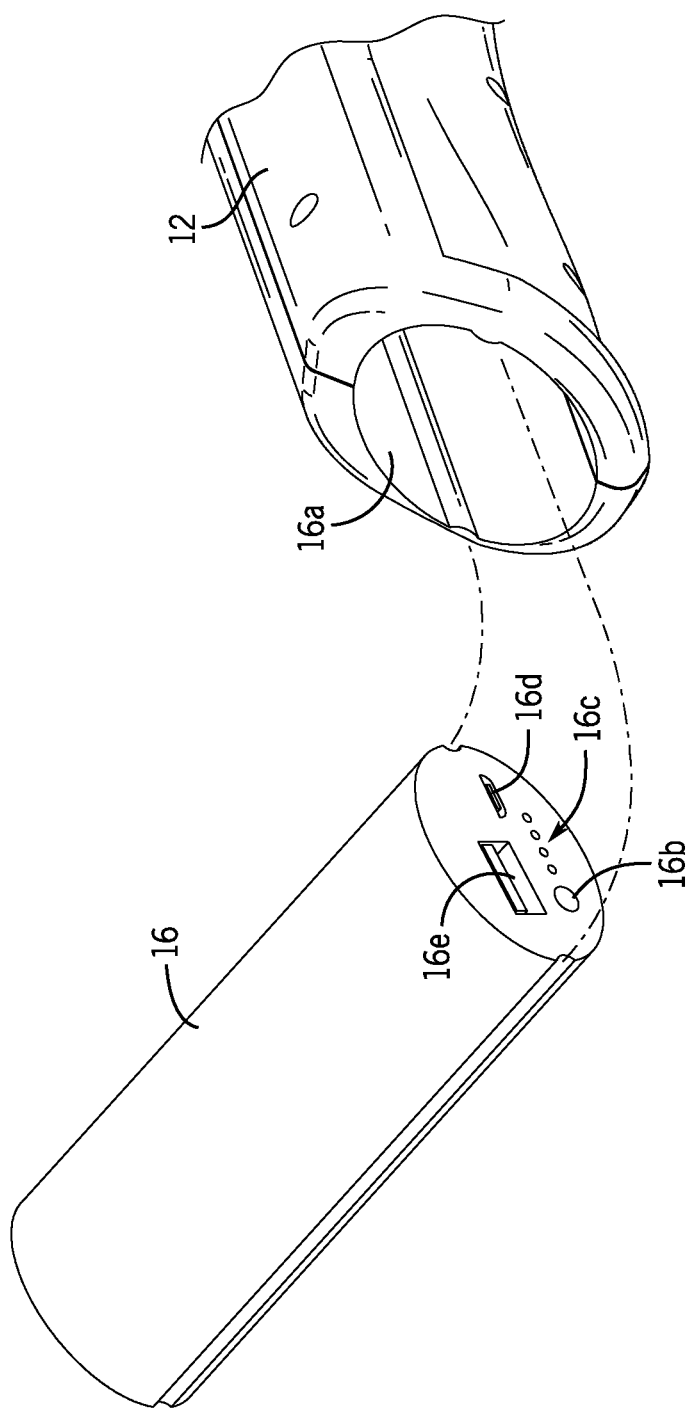

FIG. 3 conceptually illustrates a detail clamshell exploded perspective view of a battery and battery receptacle in some embodiments of the portable handheld endoscopic image and video capture and display system.

Figure 4:
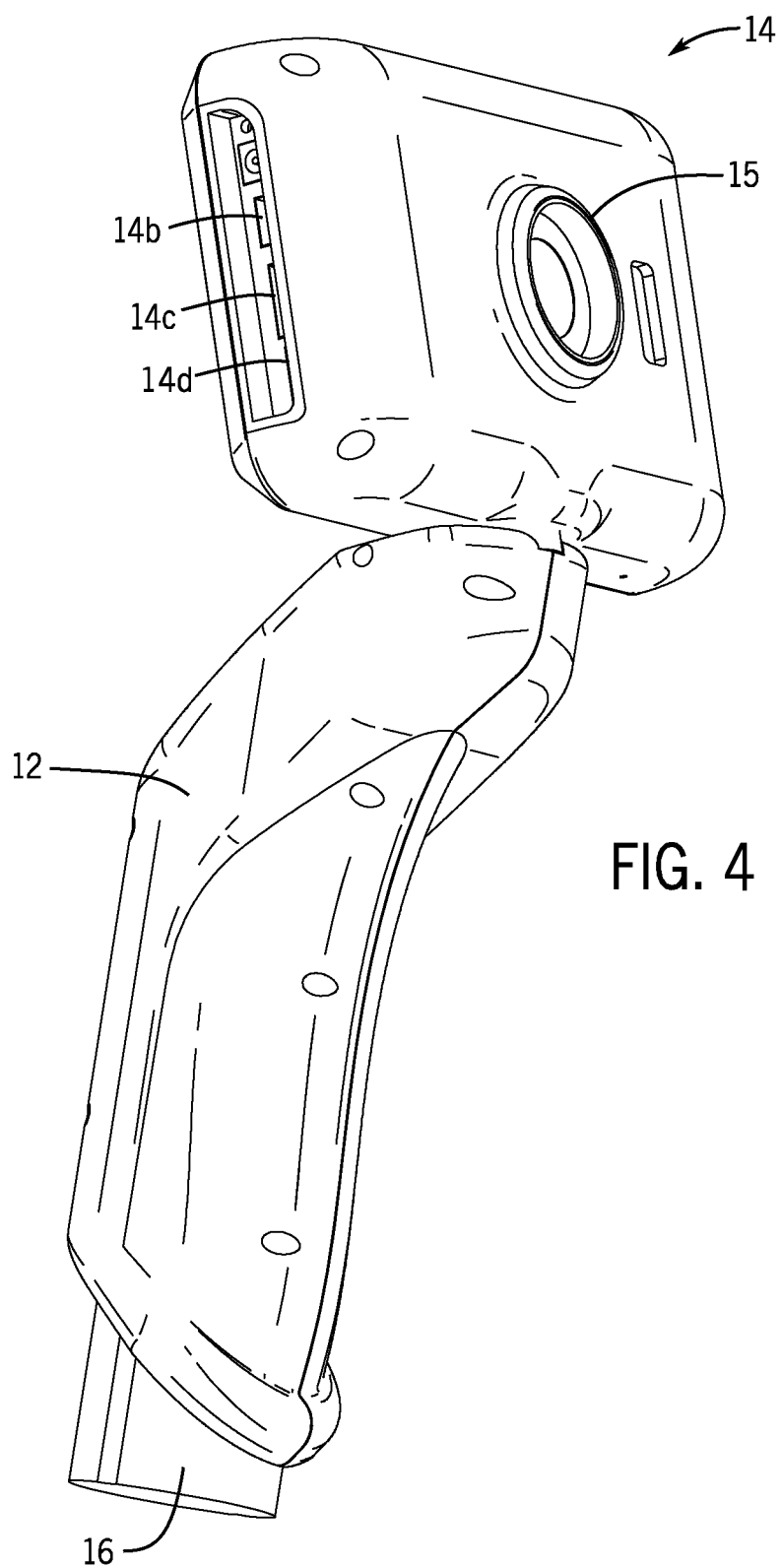

FIG. 4 conceptually illustrates another perspective view of the portable handheld endoscopic image and video capture and display system in some embodiments.

Figure 5:
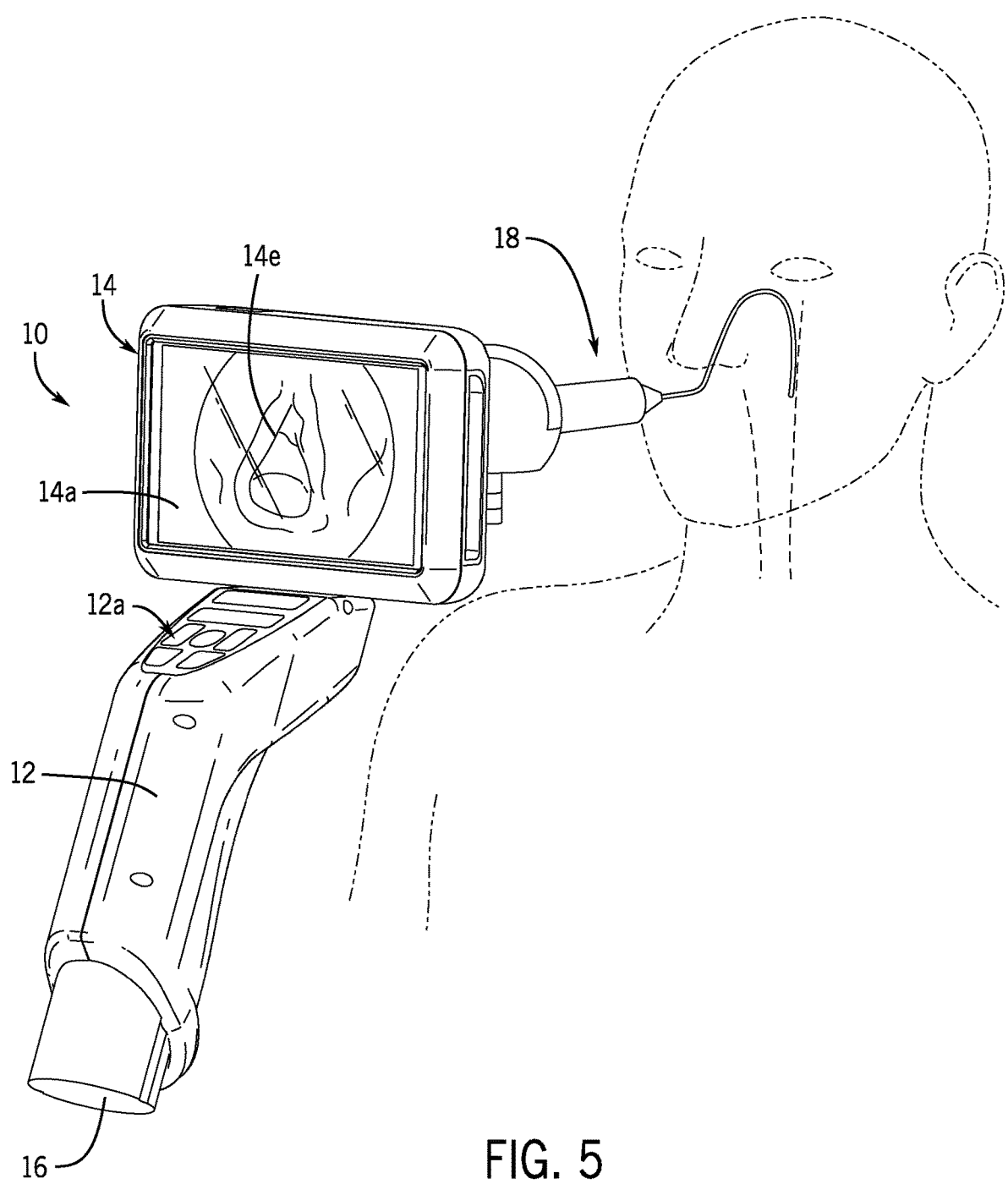

FIG. 5 conceptually illustrates a perspective view showing usage of the portable handheld endoscopic image and video capture and display system in some embodiments.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

Some embodiments provide a novel portable handheld endoscopic image and video capture and display system. In some embodiments, the portable handheld endoscopic image and video capture and display system comprises a handle, a keyboard, and a camera unit. In some embodiments, the camera unit comprises an endoscopic camera (also referred to as an "endo-camera"). In some embodiments, the camera unit comprises the endoscopic camera and a primary camera monitor (also referred to as a "display screen"). In some embodiments, the endoscopic camera attaches to an endoscope to capture images and record videos in connection with a patient. In some embodiments, the endoscopic camera captures imagery and video in high definition ("HD"). In some embodiments, the endoscopic camera captures imagery and video in ultra-high definition ("UHD" or "4K" resolution). In some embodiments, the camera unit transmits the images and videos to the camera monitor for display on the display screen while a surgeon is manipulating the endoscope. In some embodiments, the camera unit transmits the images and videos to an adaptable, detached secondary monitor while the surgeon is manipulating the endoscope.

In some embodiments, the portable handheld endoscopic image and video capture and display system is a handheld portable C-mount high definition (HD) endoscopic camera ("endo-camera"). In some embodiments, the handheld portable C-mount high definition (HD) endoscopic camera attaches to any rigid, semi-rigid, or flexible endoscope used by an operator, such as a surgeon during endoscopic surgery. In some embodiments, the handheld portable C-mount high definition (HD) endoscopic camera transmits the captured images and recorded videos to the camera monitor for display on the display screen in realtime while the endoscope is being manipulated. In some embodiments, the handheld portable C-mount HD endo-camera is self-contained and portable in a way that allows the operator (surgeon) to hold the handle in a manner that aligns a field of view of the endoscopic camera to a particular surgical field. In this way, the surgeon or other operator of the handheld portable C-mount HD endo-camera can see the surgical field directly on the display screen of the camera monitor without obtrusive and bulky video towers (camera head, CCU, light source, image clarifier, monitor and power strip), external power cords (tripping hazard), and other interfering elements of the conventional systems.

In some embodiments, the handheld portable C-mount HD endo-camera is adaptable with secondary devices via one or more input/output ports of the camera unit. In some embodiments, the handheld portable C-mount HD endo-camera is powered by a removable and rechargeable battery. In some embodiments, the removable and rechargeable battery comprises a Lithium-ion battery. In some embodiments, the Lithium-ion battery is positioned within a battery socket of the handle when powering the handheld portable C-mount HD endo-camera.

As stated above, conventional endoscopic visualization devices are bulky and tend to get in the way of a surgeon trying to position and move to ideal visual view of a patient. The conventional video tower places restrictions on the surgeon who often needs to awkwardly turn back toward an in-tower video monitor to see images and video of an endoscope which the surgeon is moving and positioning somewhere "blindly" with another hand in front. Embodiments of the portable handheld C-mount HD endo-camera described in this specification solve such problems by a fully self-contained, portable handheld C-mount HD camera that is battery powered and includes image and video output to the camera monitor (for viewing at the handheld device itself). The portable handheld C-mount HD endo-camera is capable of capturing still images and recording videos, and transmitting the captured imagery and videos to the camera monitor to visually output onto the display screen in realtime. The portable handheld C-mount HD endo-camera uses a long-lasting battery, namely, a removable and rechargeable Lithium-ion battery inserted into the handle. Images and videos can also be transmitted to a secondary device, such as a secondary detached monitor, a video and image storage device, other computing devices, etc., via mini HDMI cable and mini USB connector or stored on SD Micro card and then opened on a secondary device. The portable handheld C-mount HD endo-camera is attached directly to the endoscope so that the surgeon can see the surgical field directly on the camera monitor in their hand.

Embodiments of the portable handheld C-mount HD endo-camera described in this specification differ from and improve upon currently existing options. In particular, some embodiments differ because existing and previous means of capturing images/video require multiple bulky monitor tower/devices, a clarifier to improve image quality, multiply sources of electricity, and a monitor. These are difficult to work with for surgeons who have to maintain concentration on endoscope manipulation while watching video/image monitor that may be placed behind the surgeon or in another awkward position. In contrast, the portable handheld C-mount HD endo-camera is portable, provides C-mount HD images, is adaptable with secondary devices, and is powered with a removable Lithium-ion battery.

In addition, some embodiments of the portable handheld C-mount HD endo-camera improve upon the currently existing options because equipment maintenance on conventional (existing) video tower devices is ongoing and can be expensive. Simply replacing the devices for these conventional video tower systems is often cost prohibitive. Also, without a fully operational tower with respect to the existing conventional systems, no surgery can be performed. The monitor placement on the top of a conventional video tower system forces diverted visual attention by the surgeon. Specifically, the conventional tower systems force the surgeon to look up at the monitor and not the patient. Thus, the surgeon is required to manipulate the endoscope by viewing the monitor and not by focusing visual attention to the surgeon's own hands. Furthermore, the conventional options are lacking in other ways. For instance, accurate patient records are difficult to maintain as there is no easy method to transfer images/videos, and moving the video tower is unwieldy and prone to human error that could damage the tower system.

By contrast, the portable handheld C-mount HD endo-camera of the present disclosure provides a visual display screen in a field of view that aligns with the endoscope, since the endoscope is attached directly to the endo-camera of the camera unit. Since the camera monitor is positioned on an opposing side of the camera unit with respect to the endo-camera, the surgeon can hold the portable handheld C-mount HD endo-camera in one hand while manipulating the endoscope with the other hand, thereby ensuring that the surgeon can see both their hand/endoscope and the surgical field directly on the camera monitor. Thus, the portable handheld C-mount HD endo-camera eliminates the need for a video tower (camera head, CCU, light source, image clarifier, monitor and power strip).

The portable handheld C-mount HD endo-camera of the present disclosure may be comprised of the following elements. This list of possible constituent elements is intended to be exemplary only and it is not intended that this list be used to limit the portable handheld C-mount HD endo-camera of the present application to just these elements. Persons having ordinary skill in the art relevant to the present disclosure may understand there to be equivalent elements that may be substituted within the present disclosure without changing the essential function or operation of the portable handheld C-mount HD endo-camera.

1. C-Mount HD 1080p Camera with button pad
2. Plastic casing for camera with a grip handle and button key pad at the top of the grip
3. C-Mount Coupler attached to back of camera through the plastic casing.
4. Plastic casing for camera ("camera unit casing" or "camera casing") with a grip handle fitted with battery terminals inside a socket of the handle
5. Micro SD reader on the side surface/edge of the camera unit casing
6. Mini video out socket on the side surface/edge of the camera unit casing
7. Mini USB output on the side surface/edge of the camera unit casing
8. An SD card of sufficient data capacity (e.g., a 32 GB SD card, a 64 GB SD card, a 128 GB SD card, a 256 GB SD card, a 512 GB SD card, a 1024 GB SD card or 1 TB SD card, or larger capacity SD card).
9. Mini HDMI cable (e.g., a 6 foot mini HDMI cable)
10. Micro USB/USB cable
11. Mini USB Cable
12. 26650 lithium battery power bank with a power button, a power level indicator, a micro USB output, and USB output on one end
13. 26650 lithium battery power bank with battery terminals on one end.
14. A/C charger cord with a USB input
15. Plastic camera stand The various elements of the portable handheld C-mount HD endo-camera of the present disclosure may be related in the following exemplary fashion. The micro USB input is plugged into the power bank micro USB output and the other end is plugged into USB input to the AC charger. The power level indicator light (LEDs) flashing indicates charging. LED indicator lights fully illuminated and steady (no flashing) indicates full charged. LED indicator lights partial illuminated and steady (no flashing) indicates partially charged. The 26650 lithium battery with battery terminals on the end fits into the grip handle of the camera and is inserted to provide operational power. The SD card of sufficient data capacity (e.g., a 32 GB SD card, a 64 GB SD card, a 128 GB SD card, a 256 GB SD card, a 512 GB SD card, a 1024 GB SD card or 1 TB SD card, or larger capacity SD card) is placed into the micro SD reader along the side surface/edge of the camera unit casing. The mini HDMI cable input can be placed into the mini video out socket on the side surface/edge of the camera casing. The mini USB input may be placed into the mini USB output on the side surface/edge of the camera unit casing.

The portable handheld C-mount HD endo-camera of the present disclosure generally works by starting with a fully charged power bank battery terminal end that needs to be inserted into camera grip handle. An SD card of sufficient data capacity (e.g., a 32 GB SD card, a 64 GB SD card, a 128 GB SD card, a 256 GB SD card, a 512 GB SD card, a 1024 GB SD card or 1 TB SD card, or larger capacity SD card) needs to be inserted into the SD card reader. Connect an endoscope to the coupler. Turn on the camera power button and the power bank battery power button. To view the camera image on the display screen, just capture the image which is displayed in realtime. To view the camera image on a secondary display device (such as a detached monitor), connect the mini HDMI cable into the mini video out socket and/or connect the mini USB cable into the mini USB output on the side surface/edge of the camera casing and connected to corresponding input ports of the detached monitor. A camera stand is optional.

To make the portable handheld C-mount HD endo-camera of the present disclosure, a person would insert a fully charged power bank battery terminal end (Lithium-ion) into camera grip handle until it is fully seated. An SD card of sufficient data capacity (e.g., a 32 GB SD card, a 64 GB SD card, a 128 GB SD card, a 256 GB SD card, a 512 GB SD card, a 1024 GB SD card or 1 TB SD card, or larger capacity SD card) needs to be inserted into the SD card reader on the side surface/edge of the camera casing. Connect an endoscope to the coupler on the patient-facing surface of the camera casing. Turn on the camera power button (by selection of the corresponding button of the keyboard on the handle) and the power bank battery power button. To view the images/videos on another video device, turn off the camera and power bank battery and remove the SD card. Then access the images on another device from the SD card (e.g., for diagnostic, for demonstration or explanation, not in realtime).

To use the portable handheld C-mount HD endo-camera of the present disclosure, simply insert the power bank battery (Lithium-ion) into the grip handle and the SD card into the card read. Attach the endoscope to the coupler. Turn on the battery and the camera.

By way of example, FIG. 1 conceptually illustrates a perspective view of a portable handheld endoscopic image and video capture and display system in some embodiments. The portable handheld endoscopic image and video capture and display system 10 shown in this figure may be a portable handheld C-mount HD endo-camera, a portable handheld C-mount UHD endo-camera, a portable handheld C-mount 4K endo-camera, or another implementation of a portable handheld C-mount HD endo-camera. As shown in this figure, the portable handheld endoscopic image and video capture and display system 10 comprises a handle 12, a keyboard 12a, a camera unit 14, a display screen 14a, a battery 16, and a battery socket 16a.

In this view of the portable handheld endoscopic image and video capture and display system 10, the display screen 14a is integrated into the camera unit 14 along a back-facing surface. An opposing surface of the camera unit 14 is where a C-mount threaded coupler provides attachment of an endoscope. The C-mount threaded coupler is further described below, by reference to FIGS. 2 and 4. Attachment of an endoscope is also described below, by reference to FIG. 5.

The portable handheld endoscopic image and video capture and display system 10 also includes the keyboard 12a along a top outer surface of the handle 12. The keyboard 12a allows for easy operation of the endo-camera and includes functional buttons to power-up/power-down, capture an image, record video, an OK button, an escape/return button, and other possible options.

Additionally, the portable handheld endoscopic image and video capture and display system 10 demonstrates the battery 16 when inserted into the battery socket 16a of the handle 12. The battery 16 and battery socket 16 are further described below, by reference to FIG. 3.

Now turning to another view, FIG. 2 conceptually illustrates a detail side elevation view of the portable handheld endoscopic image and video capture and display system in some embodiments. As shown in this figure, the camera unit 14 is attached to the handle 12 and includes several input/output ports along a side surface and a C-mount threaded coupler 15 along a front-facing surface of the camera unit 14 (toward a patient). The input/output ports comprise a USB port 14b, a mini video output socket 14c, and a micro SD card slot 14d.

The camera unit 14, as shown in the figure, is attached to the handle 12 in an orientation in which the display screen 14a faces backward (away from a patient) while the C-mount threaded coupler 15 generally faces outward in the direction of the patient. When an endoscope is attached to the C-mount threaded coupler 15, a surgeon is able to hold the handle 12 in a way to view the display screen 14a, the patient, and his or her other hand while manipulating the attached endoscope.

Now referring to FIG. 3, which conceptually illustrates a detail clamshell exploded perspective view of the battery 16 and the battery socket 16a in some embodiments of the portable handheld endoscopic image and video capture and display system. Specifically, the battery 16 shown in this figure is equipped with a power button 16b, a power level indicator 16c, a micro USB input 16d, and USB 16e. When the battery 16 is inserted into the battery socket 16a and the power button 16b is on, the battery 16 provides electrical current to the portable handheld endoscopic image and video capture and display system 10. The power level indicator 16c provides a visual indication of charge status. For instance, the power level indicator 16c may flash on and off when charging and may illuminate (without flashing) when fully charged. A level of remaining charge for the battery 16 may be shown via the number of LED lights illuminated for the power level indicator 16c. The micro USB input 16d attaches to power bank to charge, while USB 16e charges the battery 16 via an AC adapter.

By way of another example, FIG. 4 conceptually illustrates another perspective view of the portable handheld endoscopic image and video capture and display system in some embodiments. In this figure, the camera unit 14 is exposed along the opposite surface of the display screen 14a. Specifically, the C-mount threaded coupler 15 is shown along this surface, which is the surface of the camera unit 14 that faces toward a patient (front-facing surface of the camera unit 14). Along the side surface of the camera unit 14 are the USB port 14b, the mini video output socket 14c, and the micro SD card slot 14d. The handle 12 is also shown in this figure, with the battery 16 installed in the battery socket 16a.

Now turning to another example, FIG. 5 conceptually illustrates a perspective view showing usage of the portable handheld endoscopic image and video capture and display system 10 in some embodiments with an endoscope attached. Specifically, the portable handheld endoscopic image and video capture and display system 10 shown in this figure includes the handle 12, the keyboard 12a, the camera unit 14, the display screen 14a, and the battery 16. Also shown in this figure is an endoscope 18, which attaches directly to the C-mount threaded coupler 15 (not shown from the view in the figure). The endoscope 18 is manipulated by a surgeon while performing endoscopic surgery on a patient. The endo-camera of the camera unit 14 is able to capture images and video and display them in realtime on the display screen 14a. This is shown in this figure by the display image 14e as seen through the endoscope down the throat of the patient. As the surgeon manipulates the endoscope 18 with one hand, the surgeon holds the handle 12 of the portable handheld endoscopic image and video capture and display system 10 in the other hand and in an orientation that allows the surgeon to maintain visual attention to the surgical field (as demonstrated by the display image 14e on the display screen 14a) and also maintain focus on the hand the surgeon is using to manipulate the endoscope 18. Accordingly, this figure demonstrates how the portable handheld endoscopic image and video capture and display system 10 enables the surgeon to operate the endoscope and maintain a visual perspective of the surgical field without ever being forced to divert visual attention from one visual perspective to the other.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

I claim:

1. A portable handheld endoscopic image and video capture and display system comprising:
   an endoscopic camera to capture images and video of a patient in connection with a C-mount endoscope;
   a display screen that visually outputs the captured images and video in realtime;

a handle comprising an outer surface, a hand grip handle section, a battery socket within the hand grip handle section, an electrical contact at an inner end of the battery socket, an opening of the outer surface at a bottom end of the hand grip handle section through which to insert a battery into the battery socket, a keyboard handle section, and a camera mounting handle section, wherein the keyboard handle section and the camera mounting handle section are aligned, wherein the hand grip handle section is bent at an angle offset from the aligned keyboard handle section and camera mounting handle section, wherein the angle offset provides an operator optimal maneuverability in a manner that aligns a field of view of the endoscopic camera to a particular surgical field;

a camera unit casing that attaches to the camera mounting handle section of the handle and houses the endoscopic camera and the display screen, wherein the camera unit casing comprises a C-mount threaded coupler to which the C-mount endoscope attaches and a patient-facing surface with an aperture in line with the endoscopic camera and at which the C-mount threaded coupler is positioned;

a plurality of input/output ports positioned along an edge of the camera unit casing, wherein the plurality of input/output ports comprise a USB port, a mini video output socket, and a micro SD card slot, wherein the USB port is positioned at a first location along the edge of the camera unit casing and is configured to output images and video captured by the endoscopic camera when a USB cable is attached to the USB port, wherein the mini video output socket is positioned at a second location along the edge of the camera unit casing and is configured to output images and video captured by the endoscopic camera when a mini HDMI cable is attached to the mini video out socket, wherein the micro SD card slot is positioned at a third location along the edge of the camera unit casing and connects to a micro SD reader/writer device that is configured to store images and video captured by the endoscopic camera on a storage device of sufficient capacity;

a power-up/power-down button; and the battery comprising a distal end, a proximal end, and a power button positioned at the proximal end of the battery, wherein the distal end of the battery partially protrudes out of the bottom end of the hand grip handle section through the opening of the outer surface when the battery is inserted into the battery socket, wherein the proximal end of the battery connects to the electrical contact at the inner end of the battery socket when the battery is fully inserted into the battery socket, wherein electrical current from the battery powers the endoscopic camera and the display screen when (i) the power-up/power-down button is turned on, (ii) the power button of the battery is turned on, (iii) the proximal end of the battery connects to the electrical contact at the inner end of the battery socket when the battery is fully inserted into the battery socket, and (iv) the battery has sufficient charge.

2. The portable handheld endoscopic image and video capture and display system of claim 1, wherein the display screen is housed opposite the patient-facing surface of the camera unit casing.

3. The portable handheld endoscopic image and video capture and display system of claim 1, wherein the endoscopic camera comprises a high definition (HD) endoscopic camera.

4. The portable handheld endoscopic image and video capture and display system of claim 3, wherein the HD endoscopic camera is positioned in line with the aperture at which the C-mount threaded coupler is positioned.

5. The portable handheld endoscopic image and video capture and display system of claim 1, wherein the battery comprises a Lithium-ion battery.

6. The portable handheld endoscopic image and video capture and display system of claim 5, wherein the battery further comprises a power level indicator that is configured to visually indicate a level of remaining charge for the battery.

7. The portable handheld endoscopic image and video capture and display system of claim 6 further comprising a keyboard that is positioned along the keyboard handle section of the handle, wherein the keyboard comprises the power-up/power-down button, an image capture button, a record video button, an OK button, and an escape/return button.

8. The portable handheld endoscopic image and video capture and display system of claim 7, wherein the storage device comprises a micro SD card.

9. The portable handheld endoscopic image and video capture and display system of claim 8, wherein the USB port comprises a mini USB port.

10. The portable handheld endoscopic image and video capture and display system of claim 9, wherein the mini USB port is a first USB port, wherein the battery further comprises a micro USB input and a second USB port.

11. The portable handheld endoscopic image and video capture and display system of claim 10, wherein the micro USB input is configured to attach to a power bank to charge the battery when the battery is removed from the battery socket.

12. The portable handheld endoscopic image and video capture and display system of claim 10, wherein the second USB port is configured to charge the battery via AC adapter.

13. The portable handheld endoscopic image and video capture and display system of claim 10, wherein the power level indicator comprises a plurality of LED lights, wherein a number of LED lights in the plurality of LED lights are configured to illuminate according to the level of remaining charge for the battery to visually indicate the level of remaining charge for the battery.

14. The portable handheld endoscopic image and video capture and display system of claim 13, wherein the power level indicator is configured to flash on and off when the battery is being charged, illuminate entirely without flashing when the battery is fully charged, and illuminate partially without flashing to indicate an approximate amount of remaining charge for the battery.

* * * * *